United States Patent [19]

Tsukaguchi

[11] Patent Number: 5,419,784
[45] Date of Patent: May 30, 1995

[54] SURFACE TREATMENT MATERIAL FOR A METALLIC BASE OF AN ARTIFICIAL TOOTH AND A SURFACE TREATMENT PROCESS USING THE SURFACE TREATMENT MATERIAL

[75] Inventor: Mamoru Tsukaguchi, Osaka, Japan

[73] Assignee: Yamamoto Kikinzoku Jigane Co., Ltd., Osaka, Japan

[21] Appl. No.: 204,496

[22] Filed: Mar. 2, 1994

[30] Foreign Application Priority Data

Mar. 23, 1993 [JP] Japan .................................. 5-062294
Sep. 30, 1993 [JP] Japan .................................. 5-245715

[51] Int. Cl.⁶ .............................................. B23K 35/34
[52] U.S. Cl. ................................... 148/24; 427/2.1
[58] Field of Search ............................ 148/24; 427/2

[56] References Cited

U.S. PATENT DOCUMENTS 4,010,048  3/1977  Tesk ...................................... 148/24
4,426,404  1/1984  Shoher ................................... 148/24

FOREIGN PATENT DOCUMENTS 47-20816  6/1968  Japan .
45-11616  4/1970  Japan .
52-5447   9/1972  Japan .
55-31817  6/1975  Japan .

*Primary Examiner*—Peter D. Rosenberg
*Attorney, Agent, or Firm*—Steven M. Rabin

[57] ABSTRACT

A surface treatment material for a metallic base of an artificial tooth is made of brazing filler metal which melts at a relatively lower temperature than melting points of components of the metallic base and which comprises fine powder of non-ferrous metal which boils at a brazing temperature and fine powder of non-ferrous metal which does not boil at the same temperature. By using the surface treatment material, a bonding strength between a facing portion of the metallic base and a formed material made of hard resin can be improved.

14 Claims, 3 Drawing Sheets

SURFACE TREATMENT MATERIAL FOR A METALLIC BASE OF AN ARTIFICIAL TOOTH AND A SURFACE TREATMENT PROCESS USING THE SURFACE TREATMENT MATERIAL

FIELD OF THE INVENTION

This invention relates to a surface treatment material for a metallic base of an artificial tooth and a surface treatment process using the surface treatment material. In particular, the invention relates to a surface treatment material which can improve a bonding strength between a facing portion of a metal frame casted as a metallic base of an artificial tooth, and a formed material made of hard resin.

BACKGROUND OF THE INVENTION

This application claims the priority of Japanese Patent Application No.5-62294(62294/1993) filed Mar. 23, 1993 and No. 5-245715(245715/1993) filed Sep. 30, 1993, which are incorporated herein by reference.

In a facing crown for an artificial front tooth, a tooth color hard resin is formed and bonded on a facing portion of a metal frame so as to get a natural appearance. But a bonding force between the hard resin and the metal frame is far from perfect. In order that the hard resin may be bonded firmly on the facing portion of the metal frame, a rugged outer surface is formed on the facing portion of the metal frame by use of retention beads, and then the rugged surface is plated with tin. By utilizing the retention beads, the surface area of the facing portion can be enlarged. And by tinning, the bonding strength of the formed material can be improved.

In spite of the combination of the retention beads and the tinning, however, the bonding strength between the hard resin and the facing portion of the metal frame is not sufficient. According to circumstances, there is a possibility that the formed material made of hard resin will peel off. In order to improve the strength of the bond between of the hard resin and the metal frame, a bonding strength accelerator such as a 4-methacryloxyethyl trimellitate anhydride will be applied before forming the hard resin on the facing portion of the metal frame. But in spite of using the bonding strength accelerator, the strength of bonding between the hard resin and the facing surface of the metal frame is not satisfactory.

This invention has been originated for overcoming the above difficulties. culties. A purpose of this invention is to provide a surface treatment material for a metallic base of an artificial tooth and a surface treatment process using such surface treatment material with high bonding strength between the facing portion of the metallic base and a hard resin formed on the metallic base.

SUMMARY OF THE INVENTION

A surface treatment material for a metallic base of an artificial tooth in this invention is made of a brazing filler metal the melting temperature of which is lower than that of the components of the metallic base, and which comprises a fine powder of non-ferrous metal which boils at a brazing temperature, and a fine powder of non-ferrous metal which does not boil at the same temperature.

A surface treatment process using the above mentioned surface treatment material will now be explained.

A proper quantity of the brazing filler metal as a surface treatment material is spread on the facing portion of the metal frame as the metallic base of an artificial tooth. And the whole metal frame is heated in a heating furnace or by some other heating means. Thereby the brazing filler metal is brazed to the facing portion of the metal frame.

Since the brazing filler metal comprises fine powder of non-ferrous metal which boils at a brazing temperature and the other fine powder of non-ferrous metal which does not boil at the same temperature, when the metal frame is heated at the above mentioned temperature with the brazing filler metal, the boiling parts and the non-boiling parts are produced on the metal frame. When the metal frame is cooled after brazing, a lot of very fine protrusions are formed on the outer surface of the surface treatment material layer. Namely the facing portion of the metal frame is finished to a rugged surface. Looking at the facing portion of the metal frame through an electron microscope, the rugged surface proves to be a complex surface having undercut concavities among the fine protrusions (see FIG. 3). When the hard resin for a crown is formed on the surface-treated facing portion of the metal frame, the hard resin can be combined with the fine protrusions and the undercut concavities on the facing surface of the metal frame mechanically. Thus, the hard resin can be strongly bonded on the facing portion of the metal frame.

That is to say, since a bonding surface area of the facing portion of the metal frame for forming the hard resin is extremely large, and since the hard resin engages with the undercut concavities of the rugged surface, the hard resin can unit with the metal frame in a body. Accordingly, the bonding between the hard resin and the facing portion of the metal frame in this invention can be made stronger than the prior art processes in which the rugged surface shaped by utilizing the retention beads is plated with tin before applying with the hard resin.

In the meantime, since the brazing filler metal layer is combined with the facing portion of the metal frame by brazing, the bonding between them is reinforced in comparison with the bonding with the former tinning layer as the surface treatment material layer. In other words, the bonding strength between the formed material made of the adhesive hard resin and the facing portion of the metal frame is improved.

The advantages of the invention are now explained. The bonding strength between the facing portion of the metal frame and the formed material made of hard resin improves by intervening the brazing filler metal layer, the outer surface of which is rugged surface has many fine undercut concavities among many fine protrusions. Therefore there is no possibility that the facing cast crown will come off unintentionally.

Moreover, since heating is the only process required to get a strong bond between the formed material made of hard resin and the facing portion of the metal frame, the surface treatment process can be simplified as compared with the former surface treatment processes having steps of applying retention beads and tinning.

Another surface treatment material of this invention is further characterized in that the brazing filler metal comprises fine powder of a base alloy that contains tin and silver and fine powder of an additional metal or alloy selected one or some from the group consisting of gold, silver, palladium, platinum, nickel and cobalt, of which liquidus points range from 600° C. to 2000° C. By using the brazing filler metal composed of the above mentioned components, a property of tin is emphasized in the outer surface of the surface treatment material layer. In this point, since tin reacts strongly with an adhesive primer, a chemical bonding between the brazing filler metal layer and the formed material has satisfactory strength.

Other treatment material of this invention is characterized in that the brazing filler metal is mixed with flux to make paste. By pasting, the surface treatment operation can be simplified.

DETAILED DESCRIPTION OF THE PREFERRED EMBODIMENTS

Table 1 below shows each percentage content of a base alloy and additional metals or alloy to compose brazing filler metals in examples 1-7 in this invention.

And these examples are compared with a former surface treatment material utilizing retention beads and plated with tin. Each of the brazing filler metals in these examples is mixed with a proper quantity of flux to make a paste.

TABLE 1

| | base alloy | additional metal | | | | flux |
| --- | --- | --- | --- | --- | --- | --- |
| | Sn—Ag (%) | Au (%) | Ag (%) | Pd (%) | Cu, In, Zn (%) | (%) |
| example 1 | 58.8 | 3.6 | 6 | 15 | 5.4 | 11.2 |
| example 2 | 67.2 | 2.4 | 4 | 10 | 3.6 | 12.8 |
| example 3 | 75.6 | 1.2 | 2 | 5 | 1.8 | 14.4 |
| example 4 | 75.6 | 0 | 10 | 0 | 0 | 14.4 |
| example 5 | 67.2 | 0 | 20 | 0 | 0 | 12.8 |
| example 6 | 58.8 | 0 | 30 | 0 | 0 | 11.2 |
| example 7 | 50.4 | 0 | 40 | 0 | 0 | 9.6 |

Figure 1:
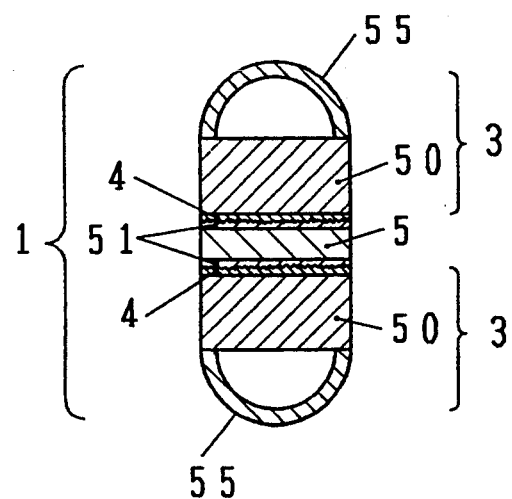
FIG. 1 is a sectional view of a test piece according to the invention.
Figure 2:
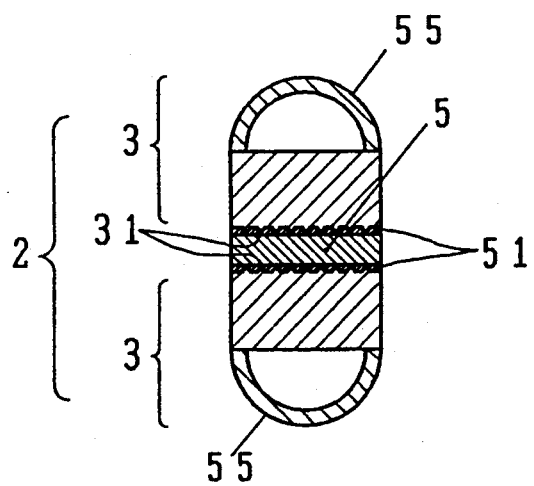
FIG. 2 is a sectional view of a test piece according to the prior art.

A test piece (1), as shown in FIG. 1, is made to test the examples 1-7 for tensile strength. A test piece (2), as shown in FIG. 2, is made as a prior art.

The test piece (1) is produced by the following process. A disc (50) of diameter 10 mm and thickness of which is 5 mm is casted from an alloy consisting of gold, silver and palladium. The same kind of the alloy material is used for a metal frame of an artificial tooth. A semicircular hook (55) for fitting with a tensile strength tester is integrated onto one surface of the disk (50) during casting. The other surface of the disc (50) is polished by a carborundum point so as to form a smooth surface. An amount 0.05 g of the brazing filler metal in the form of paste is spread on the smooth surface of the disc (50) of each of the half bodies (3,3). After that the half bodies (3,3) are heated in a heating furnace and maintained at a temperature ( for example 500° C. ) for a stated time ( for example 2 minutes ). Thereby, the brazing filler metal is brazed to the half body (3). That is, a brazing filler metal layer (4) as a surface treatment material layer is formed on the disc (50). The heating temperature is established at about the boiling point of the low liquidus point metal or alloy. For example, in the above mentioned case, a heating temperature is in the range from 400° C. to 600° C. The half bodies (3,3) are heated at a high temperature for a short time or at a low temperature for a long time.

Concretely the bodies 3 are heated at temperature and for a time duration within a range from 5 minutes when the temperature in the heating furnace is maintained at 400° C. to 30 seconds when the temperature in the heating furnace is maintained at 600° C. The best combination of the heating temperature and the heating time is within the range from 3 minutes—450° C. to 1 minute—550° C.

Next, 50 μm diameter fine particles of alumina are shot on the brazing filler metal layer (4) of the half body (3) at a pressure of 2-3 Kgf/cm$^2$ by a pencil type adherence in order to eliminate scales adhered to an outer surface of the brazing filler metal layer (4) and to ensure a stable combination between a hard resin and the brazing filler metal layer (4). And the treated surface of the half body (3) is dried up after an ultrasonic cleaning by ethanol, in 2 minutes. It is possible to select the ultrasonic cleanings time freely in the range between 2 and 3 minutes.

A thin layer (51) made of acrylic visible light ray polymerization type hard resin ( such as that sold for instance by Kuraray Co. ,Ltd. in Japan, under the trade name "Cesead" ) is polymerized and cured on the outer surface of the brazing filler metal layer (4) of each half body (3). The hard resin layer (51) of the one half body (3) is bonded to the hard resin layer (51) of the other half body (3) through an autopolymerizing resin having a good adhesive property. Thereby, a synthetic resin disc (5) of diameter 10 mm and of which thickness is 3 mm is formed between the brazing filler metal layers (4,4) of the half bodies (3,3). Namely, the test piece (1) consists of a pair of half bodies (3,3) comprising the discs (50,50), the hooks (55, 55) and the brazing filler metal layers (4, 4), the hard resin layers (51,51) polymerized and cured on the outer surface of the brazing filler metal layers (4,4), and the synthetic resin disc (5) formed between the half bodies (3,3) through the hard resin layers (51,51).

The other test piece (2) is perfected through the process that comprises the steps of forming a rugged surface (31) on one surface of the half body (3) by using the retention beads, plating with tin on the rugged surface (31), performing sandblast cleaning and ultrasonic cleaning, and polymerizing the synthetic hard resin disc (5) between the rugged surfaces (31,31) of the half bodies (3,3). The half body (3) of the test piece (2) is of the same kind as that of the test piece (1). The surface treatment processes after making the rugged surface (31) are same as those for making the test piece (1). In both the case of the test piece (1) and the case of test piece (2), the hard resin is polymerized and cured by visible light ray.

A bonding power test is operated by using a tensil tester, such as that sold by Shimazu Seisakusho Co., Ltd. in Japan, under the trade name "Auto Graph CS-500 B type". A result of the test is shown in table 2.

TABLE 2

| data number | J-1 | J-2 | J-3 | J-4 | J-5 | J-6 | J-7 | H-1 |
|---|---|---|---|---|---|---|---|---|
| bonding strength (Kgf/cm$^2$) | 205 | 201 | 210 | 169 | 202 | 194 | 175 | 70 |

Data numbers J-1 to J-7 in table 2 correspond to the above mentioned examples 1–7. The data number H-1 in the table 2 corresponds to the prior art.

The result of the test makes it obvious that the bonding strength of the examples of this invention are greatly superior to that of the prior art.

Figure 3:
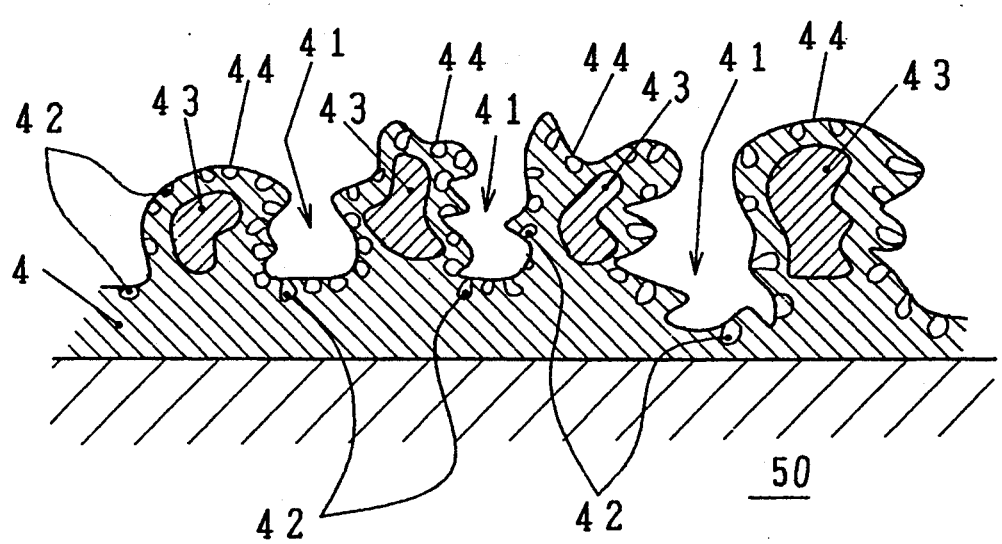
FIG. 3 is an expanded sectional view of a brazing filler metal layer (4).

Now a cross-sectional structure of the brazing filler metal layer (4) brazed on the disc (50) is shown in FIG. 3. Namely, when the base alloy (tin and silver), having a low liquidus temperature is cured after boiling for a present time duration, a great number of protrusions (44,44), including cores (43,43), are formed on the brazing filler metal layer (4) successively. Undercut minute concavities (41,41) are made among the protrusions (44,44). The above mentioned cross-sectional structure of the brazing filler metal layer (4) is formed through the following processes.

The liquidus temperature of the base alloy ranges from 200° C. to 250° C. When the base alloy is boiled for a present duration, by an air cooling effect on the boiling surface, silver or silver alloy as the additional metal or alloy solidifies into the cores (43,43). And the cores (43,43) are dispersed on the outer surface of the melting brazing filler metal layer (4). After that, when the heating is stopped, the whole brazing filler metal layer (4) is cured. Through the above mentioned steps, the protrusions (44,44) including cores (43,43), and the undercut concavities (41,41) among the protrusions (44,44), are formed on the brazing filler metal layer (4).

In the examples 1–7, very fine holes (42,42) also are formed on the outer surface of the brazing filler metal layer (4), as shown in FIG. 3. The reason why the holes (42,42) are formed can be imagined as follows. When the brazing filler metal is melted by heating at a certain temperature, the main alloy consisting of tin and silver in the melting brazing filler metal, is boiling. After that, when the brazing filler metal layer (4) is cured by cooling, the many holes (42,42) in the previously boiling parts are formed on the outer surface of the brazing filler metal layer (4).

Accordingly in the above mentioned examples, because a bonded material such as a hard resin penetrates the undercut concavities (41) and into the fine holes (42,42), a strong bond between the hard resin and the brazing filler metal layer (4) is realized.

Figure 4:
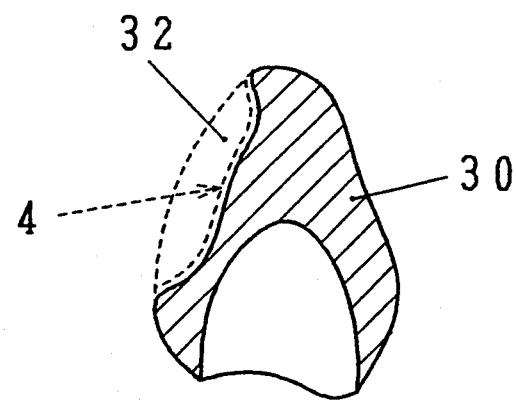
FIG. 4 is a schematic view of a facing portion of a facing cast crown.

Even if the brazing filler metal is composed of other components, if both boiling parts and non-boiling parts are produced in the heated and melted brazing filler metal, it can be used for the surface treatment material in this invention. A brazing filler metal paste, made by mixing flux with the fine powdered base alloy and additional alloy, can be spread on the facing portion (32) of the metal frame (30) as shown in FIG. 4. It is easy to produce the boiling parts and the non-boiling parts in the brazing filler metal paste evenly when the brazing filler metal is melted again by heating during the brazing.

A test on another exemplary test piece will be explained hereafter in order to confirm the effect of the surface treatment material in the present invention. A test piece (1) as an example of present invention and a test piece (2) as prior art are of the same construction as in the case of the above mentioned test pieces, but the rugged surface (31) of the test piece (2) is not plated with tin. Another test piece described below is prepared as a reference case. A disc is cast of an alloy of the same kinds as that used for the metal frame. The 250 μm of alumina in the form of particles are shot at the outer surface of the disc at the same pressure as in the case of forming the above mentioned half body (3). By shooting the particles of the alumina, many fine holes are formed on the outer surface of the disc. After that ultrasonic cleaning is performed on the rough surface of the disc. Thus, the rugged surface is formed on the outer surface of the disc, without retention beads. And the hard resin is sandwiched and cured between the rugged outer surfaces of two discs.

The bonding strength between the hard resin and the discs in each test piece is measured by means of the tensile test and of a heat cycle test. The heat cycle test is a test for inspecting deterioration with age of the bonding strength between the hard resin and the metal frame on the basis of the differences of ratio of shrinkage-thermal expansion. A concrete example of the heat cycle test will be explained now. A test piece is steeped in one vessel in which the temperature is maintained at 4° C. for one minute and then steeped in another vessel in which the temperature is maintained at 60° C. for one minuite. These two processes composed one cycle of the heat cycle test. By repeating the processes over and over, the expansion and the contraction are repeated alternately on the resin and the alloy.

Figure 5:
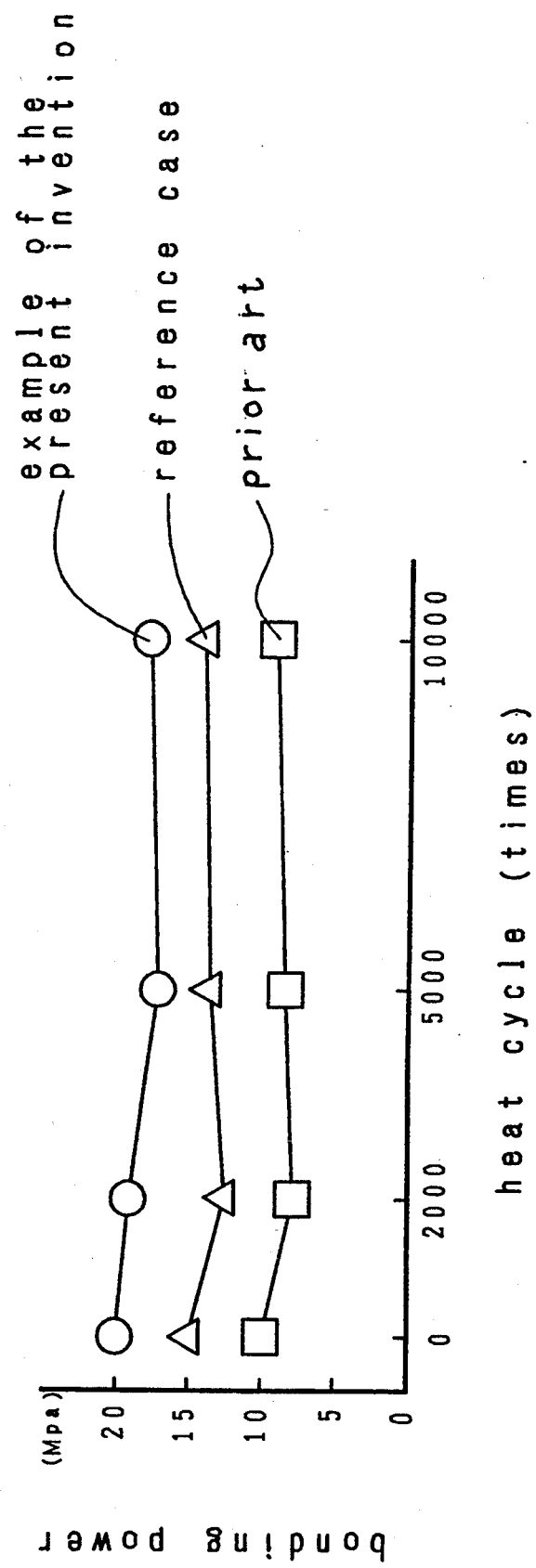
FIG. 5 is a graphical representation of a result of another test.

Test pieces of three types, namely of samples of this invention, of prior art and of a reference case were prepared by fives. The heat cycle test was performed on five test pieces of each type. And the first tensile test is given on each of the test pieces before the heat cycle test, and the second tensile test was performed on them after the 2,000th heat cycle test, the third tensile test was performed on them after the 5,000th heat cycle test, and the final tensile test was performed on them after the 10,000th heat cycle test. FIG. 5 is a graph showing averages of the bonding strength of the five test pieces of each type. FIG. 5 proves that the bonding strength of the test pieces of this invention were twice as strong as that of the prior art and is 1.4 times as strong as that of the reference case before the heat cycle test. Under all occasions, it is obvious that the test piece in this invention is superior to the others in the bonding strength.

The reason why the reference test piece using no retention beads is superior to the prior art test piece using retension beads in the bonding strengh is as follows:

In the reference test piece, since the 250 μm diameter comparatively rough particles of alumina are shot for the sandblast treatment, very fine holes are formed on the outer surface of the reference test piece and very fine protrusions are formed among the holes. The holes and the protrusions make the bonding strength rise because a sectional form of the outer surface of the reference test piece is more effective to combine with the resin more firmly than is the rugged surface by using the retention beads.

In the above mentioned examples 1-7, the very fine holes (42,42) are formed on the brazing filler metal layer (4), this layer serving as a surface treatment material layer. Compared with the brazing filler metals in the examples 1-7, the fine holes (42,42) are not formed on the brazing filler metals as shown in examples 8-10 in table 3.

TABLE 3

| | base alloy | additional metal | | | | flux |
|---|---|---|---|---|---|---|
| | Sn—Ag (%) | Au (%) | Ag (%) | Pd (%) | Cu, In, Zn (%) | (%) |
| example 8 | 42.0 | 0 | 50 | 0 | 0 | 8.0 |
| example 9 | 33.6 | 0 | 60 | 0 | 0 | 6.4 |
| example 10 | 25.2 | 0 | 70 | 0 | 0 | 4.8 |

Although the fine holes are not formed on the surface of the brazing filler metal layer in examples 8-10, the consecutive protrusions (44,44) including cores (43,43), and the undercut concavities (41,41) among the protrusions (44, 44), are formed on the brazing filler metal layer (4). Accordingly the bonding strengh (tensile strength) in examples 8-10 can be made as great as that in the examples 1-7.

Since only pure silver is used as the additional metal, and constitutes a high percentage of the content of the brazing filler metal, in the examples 8-10, when the brazing filler metals are heated to the brazing temperature, there is a small rate of boiling in parts on the surface of the brazing filler metals. So the fine rugged surface having no holes (42,42) can be formed on the outer surface of the brazing filler metal layer.

When the brazing filler metals in examples 1-7 are heated at low temperature (from 300° C. to 400° C.), though the fine holes (42,42) are not formed, a bonding strength as strong as that of the examples 8-10 can be obtained.

What I claimed is:

1. A surface treatment material for joining a dental metallic base and a dental hardened resin, comprising:
   a powder of a first non-ferrous metal that boils at a brazing temperature;
   a powder of a second non-ferrous metal that does not boil at said brazing temperature; and
   a flux, said first and second non-ferrous metals and said flux being combined in a mixture that forms a paste.

2. A surface treatment material according to claim 1, wherein said first non-ferrous metal is a first alloy.

3. A surface treatment material according to claim 2, wherein said first alloy comprises tin and silver.

4. A surface treatment material according to claim 3, wherein said second non-ferrous metal is a metal selected from the group consisting of gold, silver, palladium, platinum, nickel and cobalt.

5. A surface treatment material according to claim 2, wherein said first alloy consists of tin and silver.

6. A surface treatment material according to claim 5, wherein said second non-ferrous metal is a second alloy containing metals selected from the group consisting of gold, silver, palladium, platinum, nickel and cobalt.

7. A surface treatment material according to claim 1, wherein said second non-ferrous metal consists of an alloy containing metals selected from the group consisting of gold, silver, palladium, platinum, nickel and cobalt.

8. A surface treatment material according to claim 1, wherein said second non-ferrous metal consists of a metal selected from the group consisting of gold, silver, palladium, platinum, nickel and cobalt.

9. A surface treatment material for joining a dental metallic base and a dental hardened resin, comprising:
   a powder of a first non-ferrous metal that boils at a brazing temperature; and
   a powder of a second non-ferrous metal that does not boil at said brazing temperature; said first and second non-ferrous metals being combined in a mixture.

10. A surface treatment material according to claim 9, wherein said first non-ferrous metal is a first alloy.

11. A surface treatment material according to claim 10, wherein said first alloy comprises tin and silver.

12. A surface treatment material according to claim 11, wherein said second non-ferrous metal is a metal selected from the group consisting of gold, silver, palladium, platinum, nickel and cobalt.

13. A surface treatment material according to claim 10, wherein said first alloy consists of tin and silver.

14. A surface treatment material according to claim 9, wherein said second non-ferrous metal consists of a second alloy containing metals selected from the group consisting of gold, silver, palladium, platinum, nickel and cobalt.

* * * * *